(12) United States Patent
Romeuf et al.

(10) Patent No.: US 7,595,165 B2
(45) Date of Patent: Sep. 29, 2009

(54) METHOD OF MEASURING ACTIVATION OF EFFECTOR CELLS

(75) Inventors: Christophe de Romeuf, Lille (FR); Christine Gaucher, Sequedin (FR); Arnaud Clacet, Gondecourt (FR); Frédéric Dhainaut, Boissy-le-Sec (FR); Dominique Bourel, La Madeleine (FR); Nicolas Bihoreau, Orsay (FR); Emmanuel Nony, Antony (FR)

(73) Assignee: Laboratoire Francais du Fractionnement et des Biotechnologies, Les Ulis (FR)

( * ) Notice: Subject to any disclaimer, the term of this patent is extended or adjusted under 35 U.S.C. 154(b) by 0 days.

(21) Appl. No.: 10/527,665

(22) PCT Filed: Sep. 15, 2003

(86) PCT No.: PCT/FR03/02715
§ 371 (c)(1),
(2), (4) Date: Mar. 11, 2005

(87) PCT Pub. No.: WO2004/024768
PCT Pub. Date: Mar. 25, 2004

(65) Prior Publication Data
US 2005/0249732 A1    Nov. 10, 2005

(30) Foreign Application Priority Data
Sep. 13, 2002 (FR) ................... 02 11415
Sep. 13, 2002 (FR) ................... 02 11416

(51) Int. Cl.
*G01N 33/53* (2006.01)
*G01N 33/567* (2006.01)
*C12N 5/00* (2006.01)
*C07K 17/00* (2006.01)

(52) U.S. Cl. ............ 435/7.1; 435/7.21; 435/325

(58) Field of Classification Search ........... None
See application file for complete search history.

(56) References Cited
FOREIGN PATENT DOCUMENTS
WO    WO 01/77181    10/2001

OTHER PUBLICATIONS

Vivier et al. International Immunology. 1992, vol. 4, 11:1313-1323.*
Pullyblank et al. British Journal of Cancer 1995. 72:601-606.*
Siberl et al. Clinical Immunology 2006 118:170-179.*
Crowe, J.S., et al.; *Humanized monoclonal antibody CAMPATH-1H: myeloma cell expression of genomic constructs, nucleotide sequence of cDNA constructs and comparison of effector mechanisms of myeloma and Chinese hamster ovary cell-derived material*; Clin. Exp. Immunol. (1992) 87, 105-110.
Vivier, E., et al.; *Signaling function of reconstituted CD16: ζ : γ : receptor complex isoforms*; International Immunology (1992), vol. 4, No. 11, pp. 1313-1323.
Rouard, H., et al.; *Fc Receptors as Targets for Immunotherapy*; Intern. Rev. Immunol. (1997), vol. 16, pp. 147-185.
Lund, J., et al.; *A Protein Structural Change in Aglycosylated $I_gG3$ Correlates with Loss of huFcyR1 and of huFcyR111 Binding and/or Activation*; Molecular Immunol. (1990), vol. 27, pp. 1145-1153.
Leatherbarrow, R., et al.; *Effector Functions of a Monoclonal Aglycosylated Mouse $I_gG2_a$: Binding and Activation of Complement Component C1 and Interaction with Human Monocyte Fc Receptor*; Molecular Immunol. (1985), vol. 22, pp. 407-415.
Jefferis, R., et al.; *A Comparative Study of the N-linked Oligosaccharide Structures of Human $I_gG$ Subclass Proteins*; Intern. Biochem J. (1990), 268, pp. 529-537.
Parekh, R.B., et al.; *Association of Rheumatoid Arthritis and Primary Osteoarthritis with Changes in the Glycosylation Pattern of Total Serum $I_gG$*; Nature. (1985), vol. 316, pp. 452-457.

* cited by examiner

*Primary Examiner*—Maher M Haddad
*Assistant Examiner*—Chun Dahle
(74) *Attorney, Agent, or Firm*—Foley & Lardner LLP

(57) ABSTRACT

The invention relates to a method of measuring the activation of an effector cell belonging to the immune system, which may or may not be transformed, using a monoclonal (AcMo) or polyclonal antibody. The invention is characterised in that it consists in: bringing into contact (i) CD16 receptor-expressing cells in a reaction medium in the presence of the antibody and (ii) the antigen of said antibody, and measuring the quantity of at least one cytokine produced by the CD16 receptor-expressing cell. The invention also relates to the selection of an antibody capable of inducing the expression of cytokines and interleukins, such as IFN? or IL2 which are intended for the treatment of autoimmune and inflammatory diseases, cancers and infections by pathogens.

1 Claim, 16 Drawing Sheets

Jurkat CD16 assay: activation induced by an
anti-Rhesus D and production of IL2

Secretion of IL2 by Jurkat CD16, induced by the
antibodies DF5-EBV, DF5-YB20 and WinRho Activation of leukocytes by anti-D antibodies Release of cytokines (IL2, IFN and TNF) by leukocytes that are antibody-activated in the presence of their target Induction of cytokine (IFN, TNF) secretion by NK cells activated by anti-D antibodies and their target (LFB-R297-RBC)

Release of cytokines (IFN, TNF) by NK cells that are antibody-activated in the presence of their target (LFB-R297-RBC)

Release of IL2 from Jurkat CD16, induced by anti-CD20 antibodies

Secretion of IL2 by Jurkat CD16 activated by the anti-CD20 CAT 13 or C273

Release of IL2 from Jurkat CD16, induced by anti-D antibodies

Secretion of IL2 by Jurkat CD16 activated by various anti-Rhesus D antibodies

Correlation between the ADCC assay in the presence of Tegeline and the secretion of IL2 by Jurkat CD16.
Antibody: LFB-R297

Secretion of TNF alpha by NK cells, induced by the
anti-CD20 and anti-HLA-DR antibodies expressed in CHO
and YB2/0 (324 03 082)

Secretion of IFN gamma by NK cells, induced by the
anti-CD20 and anti-HLA-DR antibodies expressed in CHO
and YB2/0 (324 03 082)

METHOD OF MEASURING ACTIVATION OF EFFECTOR CELLS

BACKGROUND OF THE INVENTION

FIELD OF THE INVENTION

The present invention relates to a method for measuring the activation of an effector cell belonging to the immune system, or modified in vitro, by means of a monoclonal (MoAb) or polyclonal antibody, characterized in that it comprises bringing CD16 receptor-expressing cells into contact in a reaction medium in the presence of the antibody and of the antigen for said antibody, and measuring the amount of at least one cytokine produced by the CD16 receptor-expressing cell. The invention also relates to the selection of antibodies having the characteristic of inducing the expression of cytokines and of interleukins, in particular IFNγ or IL-2.

Immunotherapy by means of polyclonal or monoclonal antibodies is in the process of becoming one of the most important aspects of medicine. On the other hand, the results obtained in clinical trials appear to be contrasting. In fact, the monoclonal antibody may prove to be insufficiently effective. Today, research is directed toward the immunoglobulin Fcγ fragment in order to improve antibody properties. In the end, this should make it possible to obtain antibodies which interact with and activate the receptors of effector cells (macrophage, T lymphocyte and NK cell).

The biological activity of certain immunoglobulins G is dependent on the structure of the oligosaccharides present on the molecule, and in particular on its Fc portion. The IgG molecules of all human and murine subclasses have an N-oligosaccharide attached to the $CH_2$ domain of each heavy chain (at residue Asn 297 for human IgGs). The influence of this glycan residue on the ability of the antibody to interact with effector molecules (Fc receptors and complement) has been demonstrated. Inhibiting glycosylation of a human IgG1, by culture in the presence of tunicamycin, results for example in a 50-fold decrease in the affinity of this antibody for the FcγR1 receptor present on monocytes and macrophages (Leatherbarrow et al., 1985). Binding to the FcγRIII receptor is also affected by the loss of carbohydrates on IgG, since it has been described that an unglycosylated IgG3 is incapable of inducing ADCC-type lysis by the FcγRIII receptor on NK cells (Lund et al., 1990).

However, beyond the necessary presence of these glycan residues, it is more precisely the heterogeneity of their structure which can result in differences in the ability to engage effector functions. Galactosylation profiles that are variable according to individuals (human serum IgG1s) have been observed. These differences probably reflect disparities between the activity of galactosyltransferases and other enzymes between the cellular clones of these individuals (Jefferis et al., 1990). Although this normal heterogeneity of post-translational processes generates various glycoforms (even in the case of monoclonal antibodies), it can result in atypical structures associated with certain pathological states such as rheumatoid arthritis or Crohn's disease, for which a considerable proportion of agalactosylated residues has been demonstrated (Parekh et al., 1985).

DESCRIPTION OF RELATED ART

Faced with the complexity posed by the relationship that exists between the various glycan structures and the activity of antibodies, it would be useful to be able to rapidly discriminate which antibodies are effective, and thus make it possible to select cell lines producing antibodies having greater effectiveness or specific properties in the activation or inhibition of certain components of the immune system.

In application FR 0004685 of Apr. 12, 2000 (LFB), we have described a novel method for preparing a monoclonal antibody capable of activating effector cells expressing FcγRIII. In this method, monoclonal antibodies originating from hybridomas or from transfected lines are tested in a reaction mixture comprising the target cells of said antibodies, effector cells comprising FcγRIII-expressing cells, and polyvalent IgGs. Thus, it is possible to determine the percentage lysis of the target cells and to select monoclonal antibodies which activate the effector cells, causing significant lysis of the target cells (FcγRIII-type ADCC activity). For example, the Fab portion of the anti-D antibody will bind to the Rhesus D antigen carried by red blood cells. Subsequent to this binding, its Fc portion then binds to the Fc gamma RIII receptor, or CD16, of the effector cell (NK cell). This "sandwich" induces the secretion of chemical substances such as performs which will lyse the red blood cell. This is therefore an antibody-dependent cellular cytotoxicity (ADCC). In order to be close to physiological conditions, the test is carried out in the presence of human polyvalent immunoglobulins.

SUMMARY OF THE INVENTION

In the context of the invention, it has been found that the binding of an antibody to its ligand can induce activation of CD16-transfected Jurkat cells, inducing IL-2 secretion. A strong correlation is observed between the secretion of IL-2 by Jurkat CD16 and the CD16-mediated ADCC activity of the effector cells. In addition, we have observed that the same antibody directed against a given antigen is completely ineffective when it is produced in mouse myeloma lines, whereas it is found to be very effective when it is produced in other cell lines.

The problem is therefore to determine the ability of a given antibody to stimulate the production of cytokines by effector cells, and the consequences of such an activation according to the nature of the cytokines released.

The invention therefore proposes the use of antibodies selected using a Jurkat CD16 test, by measuring secreted IL-2 or other cytokines, which makes it possible to guarantee the biological activity of said antibodies for therapeutic use.

Figure 15:
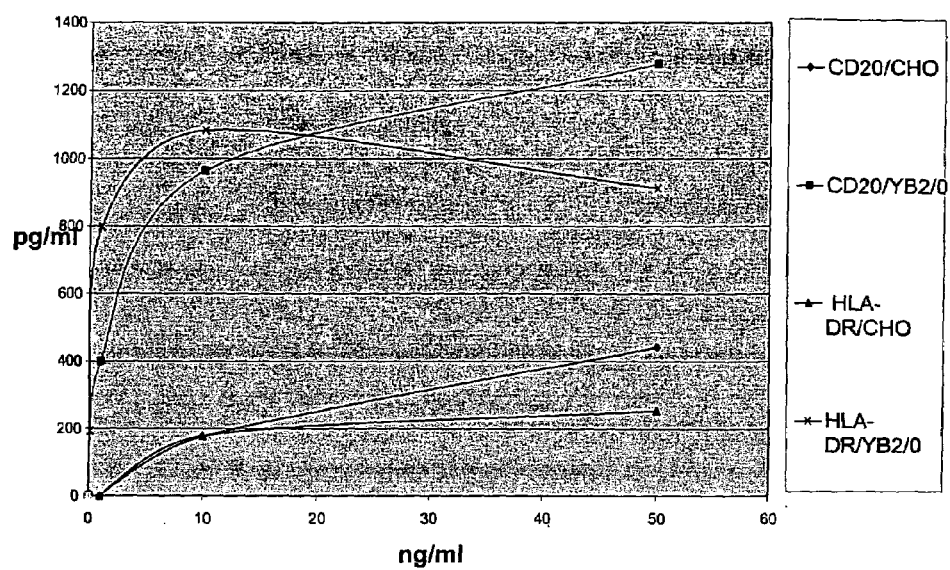

FIG. 15: Secretion of TNF alpha by NK cells, induced by the anti-CD20 and anti-HLA-DR antibodies expressed in CHO and YB2/0 (324 03 082).

Figure 16:
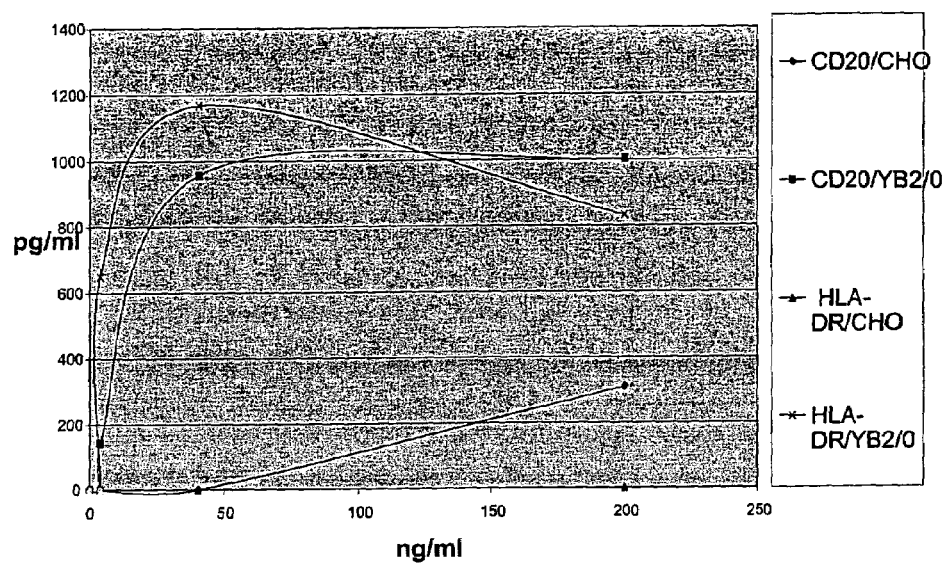

FIG. 16: Secretion of IFN gamma by NK cells, induced by the anti-CD20 and anti-HLA-DR antibodies expressed in CHO and YB2/0 (324 03 082).

DESCRIPTION

Thus, in a first aspect, the present invention relates to a method for measuring the activation of an effector cell belonging to the immune system, which may or may not be transformed, by means of a monoclonal (MoAb) or polyclonal antibody characterized in that it comprises bringing CD16 receptor-expressing cells into contact in a reaction medium in the presence of the antibody and of the antigen for said antibody, and measuring the amount of at least one cytokine produced by the CD16 receptor-expressing cell.

The term "transformed cell" is intended to mean a cell that has been genetically modified so as to express a receptor, in particular the CD16 receptor.

In general, for selecting the antibodies, use is made of a Jurkat-type line or another line transfected with an expression vector encoding the Fc receptor, including CD16, CD32 and CD64, as effector cell. Preferably, a Jurkat line transfected with an expression vector encoding the CD16 receptor is used as effector cell. This line is particularly advantageous since it is immortalized and develops indefinitely in culture media.

Among the cytokines that may be quantified, it is possible to measure the production of at least one cytokine selected from IL-1, IL-2, IL-3, IL-4, IL-5, IL-6, IL-7, IL-8, IL-9, IL-10, etc., TNFα, TGFβ, IP10 and IFNγ. The interleukin IL-2 may advantageously be chosen.

The amount of cytokine produced is a marker for activation or for inhibition of effector cells.

Preferably, the amount of interleukin IL-2 secreted reflects the quality of the antibody bound by the CD16 receptor as regards its antigen-binding integrity (Fc function) and effectiveness (antigenic site). The measurement of the amount of IL-2 is correlated with an ADCC-type activity.

In another aspect, the invention relates to a method for evaluating the effectiveness of a monoclonal or polyclonal antibody, characterized in that it comprises bringing CD16 receptor-expressing effector cells of the immune system, which may or may not be transformed, into contact in a reaction medium in the presence of an antibody and of the antigen for said antibody, and measuring the amount of at least one cytokine produced by the CD16 receptor-expressing cell.

This method is particularly suitable for evaluating the effectiveness of a monoclonal or polyclonal antibody having an anti-human red blood cell Rh D specificity.

In another aspect, the invention relates to a method for evaluating the ability of a cell to produce an effective monoclonal antibody, characterized in that it comprises bringing CD16 receptor-expressing effector cells of the immune system, which may or may not be transformed, into contact in a reaction medium in the presence of an antibody and of the antigen for said antibody, and measuring the amount of at least one cytokine produced by the CD16 receptor-expressing cell.

This method can be implemented for cells used for the production of therapeutic antibodies, such as CHO, YB2/0, human lymphoblastoid cells, insect cells and murine myeloma cells.

This method may also be applied to the evaluation of MoAb production by transgenic plants or transgenic mammals.

In a complementary aspect, the invention is directed toward a method for evaluating the effectiveness and the integrity of polyclonal antibodies after one or more purification steps, characterized in that it comprises bringing CD16 receptor-expressing effector cells of the immune system, which may or may not be transformed, into contact in a reaction medium in the presence of the purified antibody and of the antigen for said antibody, and measuring the amount of at least one cytokine produced by the CD16 receptor-expressing cell.

The methods described above can optionally be carried out in the presence of human immunoglobulins (IVIgs).

By way of example, antibodies for which an increase of more than 100%, 250%, 500% or 1000% in the amount of IL-2 release is observed compared with the control in the absence of antibody, or a given antibody as negative reference, will be selected.

The invention is also directed toward the use of the method described above, for selecting antibodies that are effective for a therapeutic treatment. For example, the antibody selected may be an anti-D. It may also be intended for the treatment of autoimmune and inflammatory diseases, cancers and infections with pathogenic agents.

The invention also relates to a kit for evaluating the biological activity of an antibody, comprising means and reagents required and CD16 receptor-expressing effector cells for carrying out the method described above making it possible to assay at least one cytokine, in particular IL-2, IFN and TNF.

In addition, this assay may also comprise an ADCC assay. In this respect, the invention relates to a method for selecting an optimized chimeric, humanized or human monoclonal antibody, characterized in that it comprises bringing CD16 receptor-expressing cells into contact in a reaction medium in the presence of the antibody and of the antigen for said antibody, and measuring the amount of at least one cytokine produced by the CD16 receptor-expressing cell.

In a particular embodiment, the antibody of the invention is capable of inducing the secretion of at least one cytokine by a leukocytic cell, in particular of the NK (natural killer) family, or by cells of the monocyte-macrophage group. In general, for selecting the antibodies, use is made of a Jurkat-type line or another line transfected with an expression vector encoding the Fc receptor, including CD16, CD32 and CD64, as effector cell. Preferably, for selecting the antibodies, a Jurkat line transfected with an expression vector encoding the CD16 receptor is used as effector cell. This line is particularly advantageous since it is immortalized and develops indefinitely in culture media. The amount of interleukin IL-2 secreted reflects the quality of the antibody bound by the CD16 receptor as regards its antigen-binding integrity (Fc function) and effectiveness (antigenic site).

In another embodiment, the optimized antibody can be prepared after having been purified and/or modified ex vivo by modification of the glycan structure of the Fc fragment. To this effect, any suitable chemical, chromatographic or enzymatic means can be used to modify the glycan structure of the antibodies.

In another embodiment, the antibody can be produced by cells of rat myeloma lines, in particular YB2/0 and its derivatives. Other lines may be selected for their properties of producing the antibodies defined above.

Human lymphoblastoid cells, insect cells and murine myeloma cells may, for example, be tested. The selection may also be applied to the evaluation of the antibodies produced by transgenic plants or transgenic mammals. To this effect, production in CHO serves as a reference (CHO being used for medicament antibody production) for comparing and selecting the production systems resulting in the antibodies according to the invention.

The general glycan structure of antibodies is of the biantennary type, with short chains, a low degree of sialylation, nonintercalated terminal attachment point mannoses and GlcNAcs, and a low degree of fucosylation. In these antibodies, the intermediate GlcNAc content is non zero. For example, use may be made of compositions of antibodies having a content greater than 60%, preferably greater than 80% for the G0+G1+G0F+G1F forms, it being understood that the G0F+G1F forms are less than 50%, preferably less than 30%. These compositions can be obtained with rat myeloma lines, for example with the YB2/0 line.

In a second aspect, the invention is directed toward the use of an antibody described above, for preparing a medicament intended to induce the secretion of at least one cytokine by an effector cell belonging to the immune system, said antibody being characterized in that it can be obtained by means of a method of selection comprising bringing CD16 receptor-expressing effector cells of the immune system, which may or may not be transformed, into contact in a reaction medium in the presence of the test antibody and of the antigen for said antibody, and measuring the amount of at least one cytokine produced by the CD16 receptor-expressing cell.

Preferably, for selecting the antibodies, a Jurkat line transfected with an expression vector encoding the CD16 receptor is used as effector cell. Said released cytokines are interleukins, interferons and tissue necrosis factors (TNF). Thus, the antibody selected has the ability to induce the secretion of at least one cytokine chosen from IL-1, IL-2, IL-3, IL-4, IL-5, IL-6, IL-7, IL-8, IL-9, IL-10, etc., TNFa, TGFβ, IP10 and IFNγ, by the CD16 receptor-expressing effector cells of the immune system.

Preferably, the antibody selected has the ability to induce the secretion of IL-2 by the CD16 receptor-expressing effector cells of the immune system. The amount of interleukin IL-2 secreted reflects the quality of the antibody bound by the CD16 receptor as regards its antigen-binding integrity (Fc function) and effectiveness (antigenic site). The measurement of the amount of IL-2 is correlated with an ADCC-type activity.

The selection can take place on antibodies produced by cells commonly used for the production of therapeutic antibodies, such as CHO, YB2/0, human lymphoblastoid cells, insect cells and murine myeloma cells. The selection may also be applied to the evaluation of antibodies produced by transgenic plants or transgenic mammals.

Preferably, the invention is directed toward the use of an antibody produced by a rat myeloma line, for example with the YB2/0 line, for preparing a medicinal product intended to induce the secretion of at least one cytokine by an effector cell belonging to the immune system. In this respect, the invention relates to the use of an antibody having a biantennary-type glycan structure, with short chains, a low degree of sialylation, nonintercalated terminal attachment point mannoses and GlcNAcs and a low degree of fucosylation, for preparing a medicinal product intended to induce the secretion of at least one cytokine by an effector cell belonging to the immune system. In this antibody, the intermediate GlcNAc content is non zero. For example, use may be made of compositions of antibodies with a content of greater than 60%, preferably greater than 80% for the G0+G1+G0F+G1F forms, it being understood that the G0F+G1F forms are less than 50%, preferably less than 30%.

In a particular embodiment, the antibody selected is capable of inducing the secretion of at least one cytokine by a leukocytic cell, in particular of the NK (natural killer) family, or by cells of the monocyte-macrophage group.

The invention also relates to the use of the selected antibodies described above that are specific for an antigen which originates from a pathological cell or from an organism that is pathogenic for humans.

This antibody is a monoclonal or polyclonal antibody.

For example, the antibody is a monoclonal or polyclonal antibody having anti-human red blood cell Rhesus specificity.

The antibody according to the invention may also be an antibody directed against viruses that are pathogenic for humans, against malignant tumor antigens or against the antigens of a bacterium or of a parasite that is pathogenic for humans.

Advantageously, the antibody selected shows an increase of more than 100%, 250%, 500% or 1000% in the amount of IL-2 release compared with the control in the absence of antibody or in the presence of a given antibody as negative reference. The method described above can optionally be carried out in the presence of human immunoglobulins (IVIgs). For comparison, homologous antibodies produced in CHO cells, or else commercially available reference antibodies, may be used.

In a supplementary aspect, the invention is directed toward the use of said selected antibodies as a therapeutic support in human medicine, in particular for producing a medicinal product intended for the treatment of autoimmune and inflammatory diseases, cancers and infections with pathogenic agents.

LEGENDS

Figure 1:
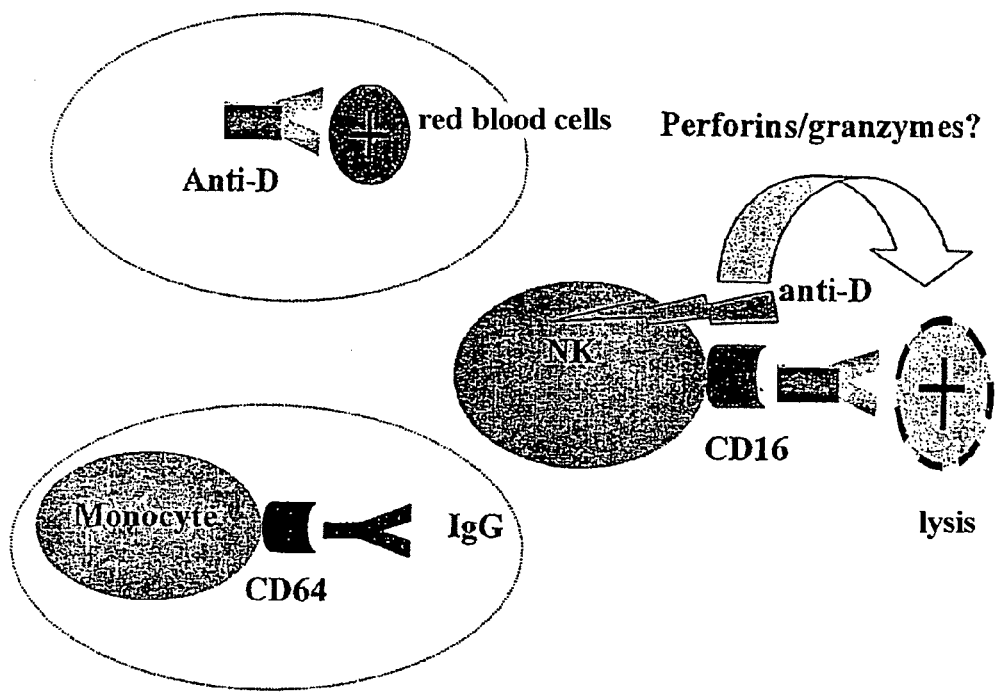
FIG. 1 is a description of the MNC ADCC assay.

FIG. 1: Description of the MNC ADCC assay

Mononuclear cells in the presence of Tegeline (IVIg) are incubated with the anti-Rhesus D antibodies and Rhesus+red blood cells (target). After an overnight period at 37° C., the red blood cell lysis is measured by evaluating the amount of hemoglobin released into the reaction medium.

Figure 2:
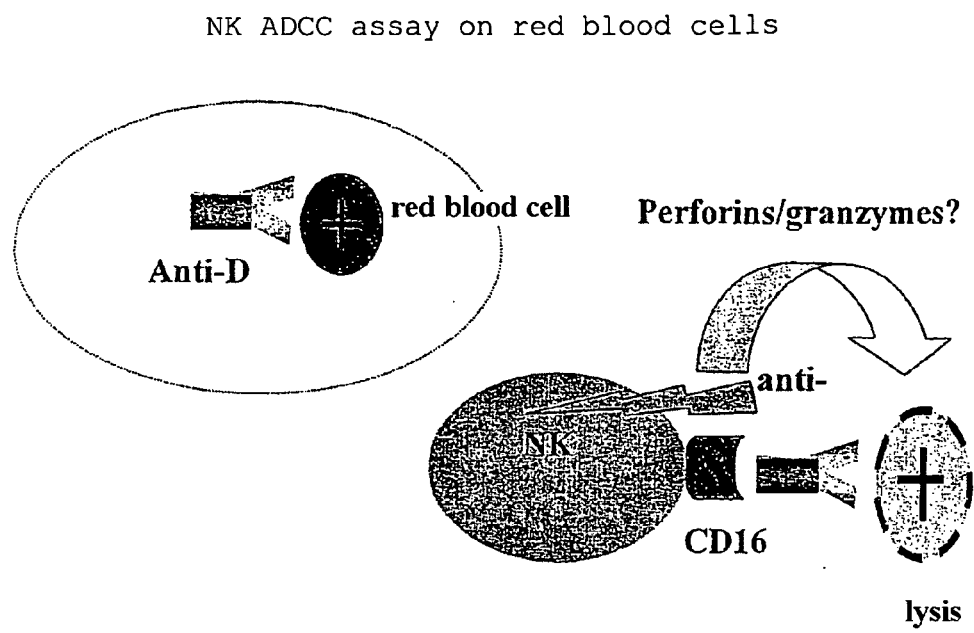
FIG. 2 is a description of the NK ADCC assay.

FIG. 2: Description of the NK ADCC assay

Purified NK cells are incubated with the anti-Rhesus D antibodies and Rhesus+red blood cells (target). After an overnight period at 37° C., the red blood cell lysis is measured by evaluating the amount of hemoglobin released into the reaction medium.

Figure 3:
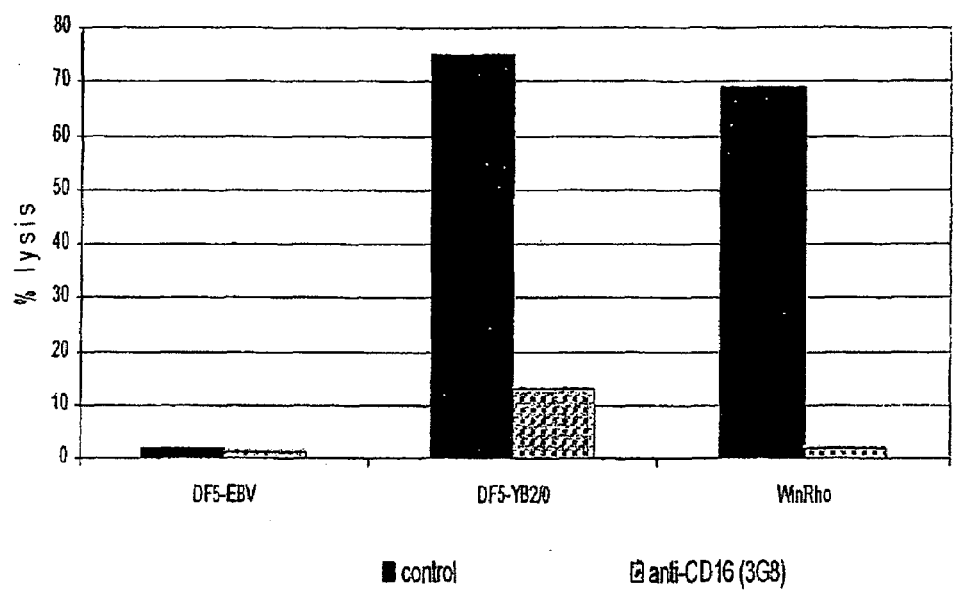
FIG. 3 is a description of the NK ADCC and resulting inhibition of the anti-CD16 "3G8".

FIG. 3: NK ADCC results and inhibition with the anti-CD16 "3G8"

The anti-D antibodies DF5-EBV (expressed by the EBV-immortalized B cell) and DF5-YB2/0 (expressed by the YB2/0 cell) are compared with the polyclonal antibody WinRho with respect to their ability to induce lysis of Rhesus D red blood cells in the presence of NK cells. The inhibition of the ADCC is studied in the presence of the anti-CD16 3G8.

Figure 4:
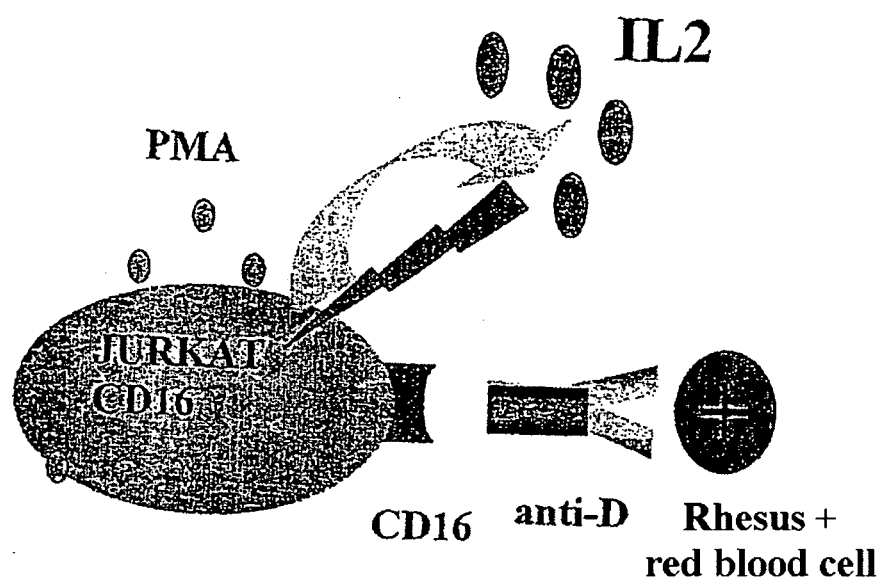
FIG. 4 is a description of the Jurkat CD16 assay.

FIG. 4: Description of the Jurkat CD16 assay

Jurkat CD16 cells are mixed with various anti-D antibodies in the presence of Rhesus+red blood cells and of PMA. After an overnight incubation period, the release of IL-2 into the supernatant is quantified by ELISA.

Figure 5:
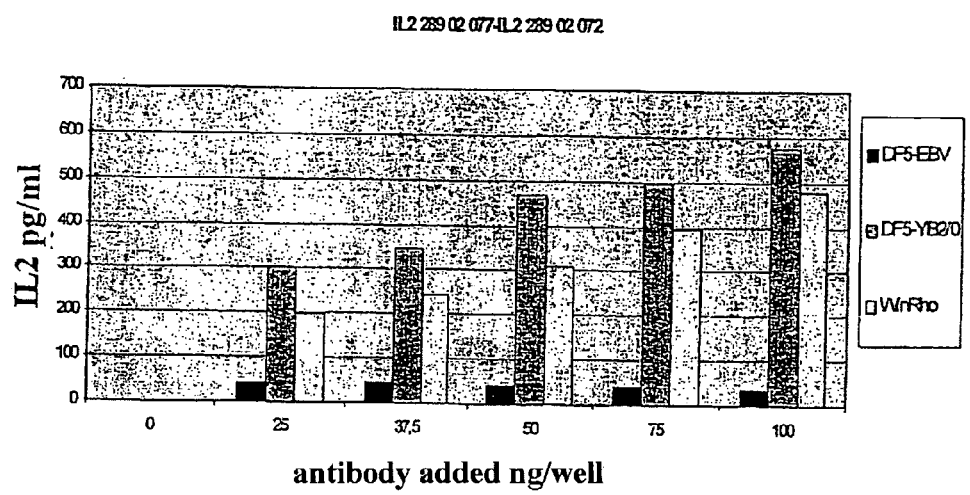
FIG. 5 shows results of the Jurkat CD16 assay.

FIG. 5: Results of the Jurkat CD16 assay

Comments: the antibodies that are positive in ADCC-NK induce secretion of IL-2 in the presence of Jurkat CD16 and of their target.

Figure 6A:
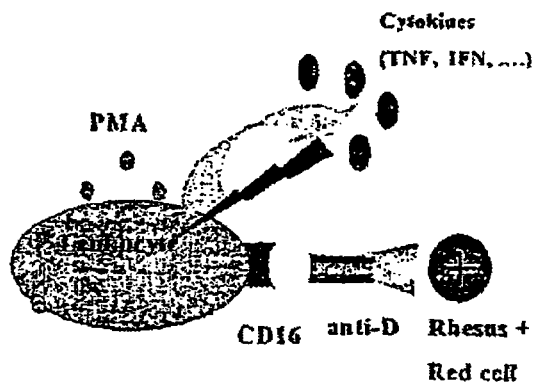
FIG. 6 shows release of cytokine (IL-2, INF and TNF) by leukocytes that are antibody activated in the presence of their target.
Figure 6B:
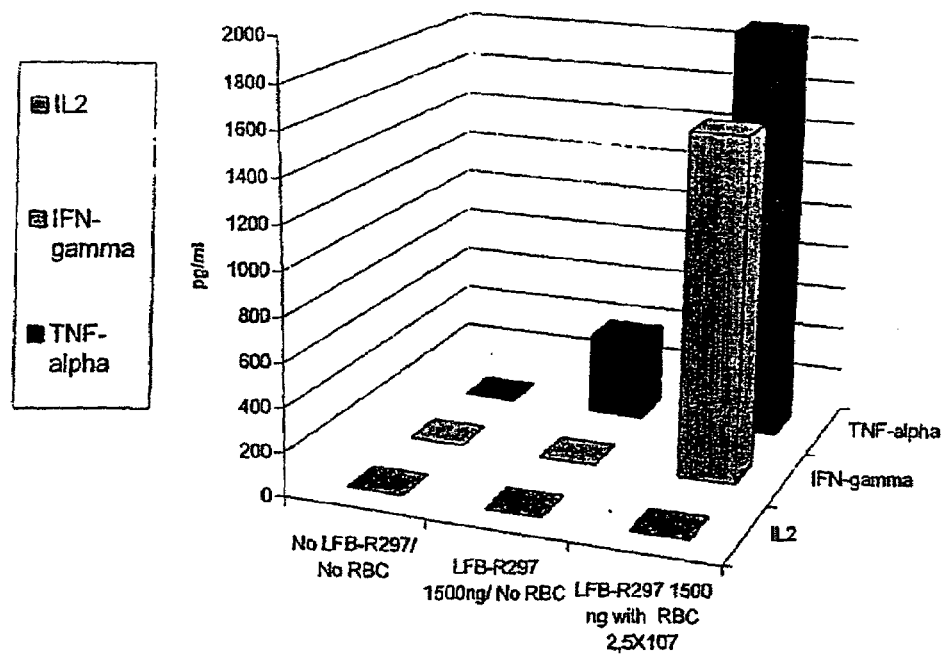

FIG. 6: Release of cytokine (IL-2, IFN and TNF) by leukocytes that are antibody-activated in the presence of their target A—Leukocyte activation scheme B—The leukocytes were incubated with various antibodies in the presence of red blood cells. After an overnight incubation period, the release of TNFa and IFNγ into the supernatant was quantified by ELISA.

Figure 7A:
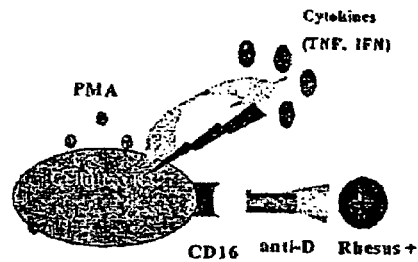
FIG. 7 shows release of cytokine (IFN, TNF) by NK cells that are antibody-activated in the presence of their target (LFB-R297-RBC).
Figure 7B:
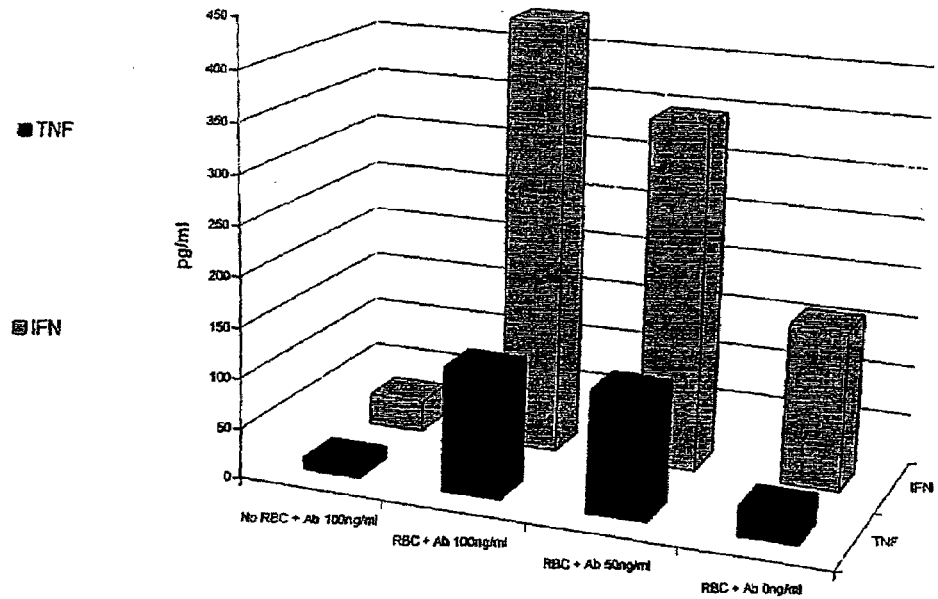

FIG. 7: Release of cytokine (IFN, TNF) by NK cells that are antibody-activated in the presence of their target (LFB-R297-RBC)

A—NK cell activation scheme.

B—Purified NK cells were mixed with various anti-D antibodies in the presence of Rhesus+red blood cells. After an overnight incubation period, the release of TNFa and of IFNγ into the supernatant was quantified by ELISA.

Figure 8A:
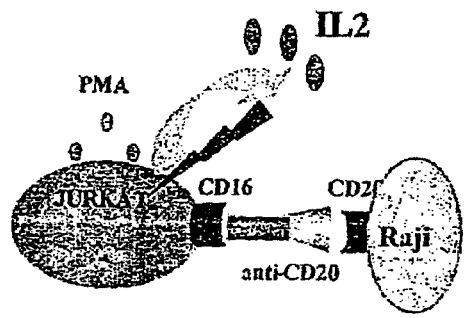
FIG. 8 shows release of IL2 by Jurkat CD16 activated by an anti-CD20.
Figure 8B:
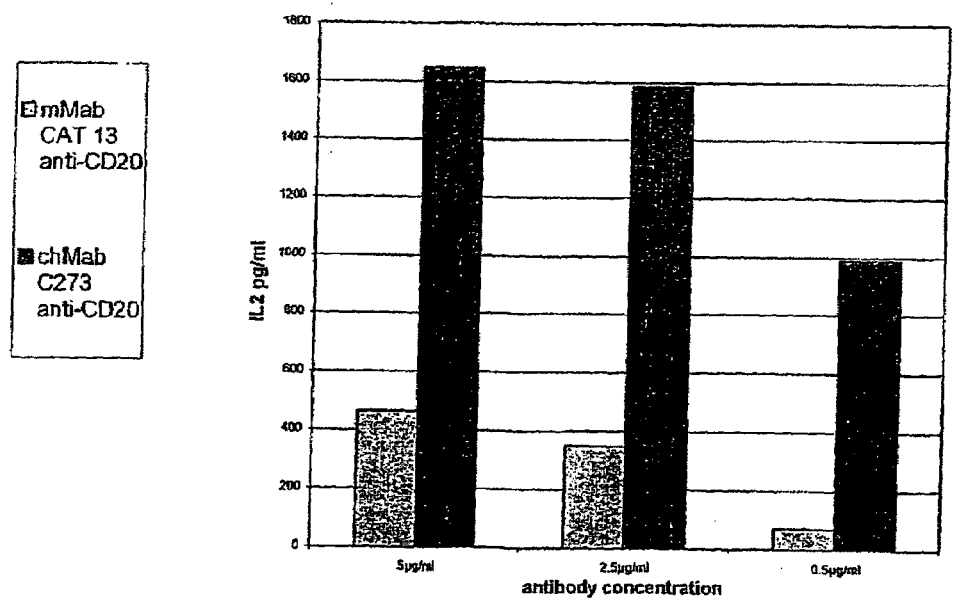

FIG. 8: Release of IL-2 by Jurkat CD16 activated by an anti-CD20

A—Jurkat cell activation scheme.

B—Jurkat CD16 cells were mixed with various anti-CD20 antibodies (murine antibody CAT13 and chimeric antibody C273) in the presence of Raji cells and of PMA. After an overnight incubation period, the release of IL-2 into the supernatant was quantified by ELISA.

Figure 9A:
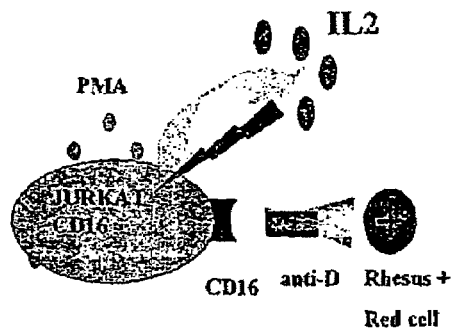
FIG. 9 shows release of IL2 by Jurkat CD16 activated by an anti-D.
Figure 9B:
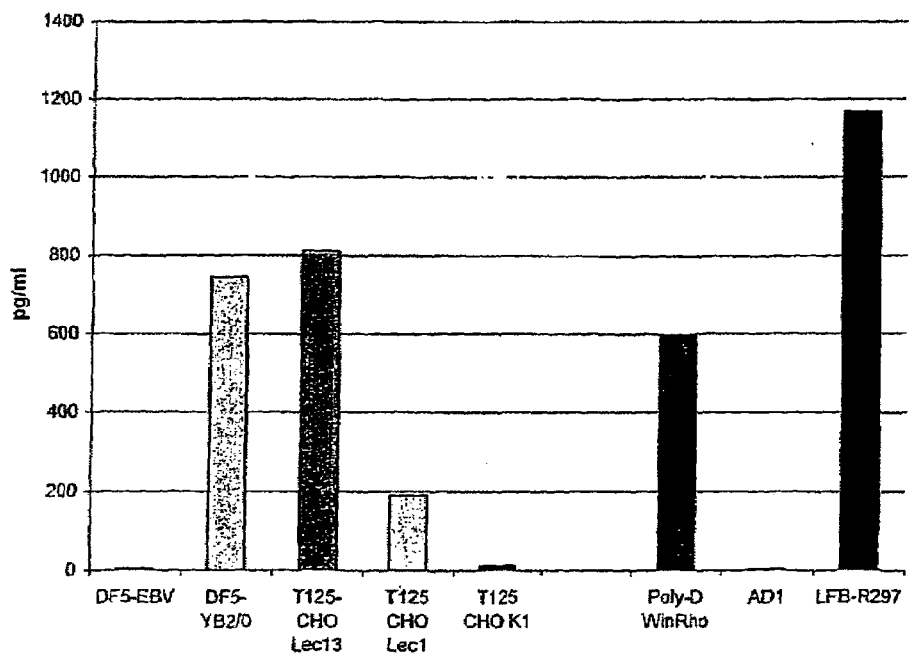

FIG. 9: Release of IL-2 by Jurkat CD16 activated by an anti-D

A—Jurkat cell activation scheme.

B—Jurkat CD16 cells were mixed with various anti-D antibodies in the presence of Rhesus+red blood cells and of PMA. After an overnight incubation period, the release of IL-2 into the supernatant was quantified by ELISA. DF5 expressed in YB2/0 and T125 expressed in CHO Lec13 induce strong secretion of IL-2.

Figure 10:
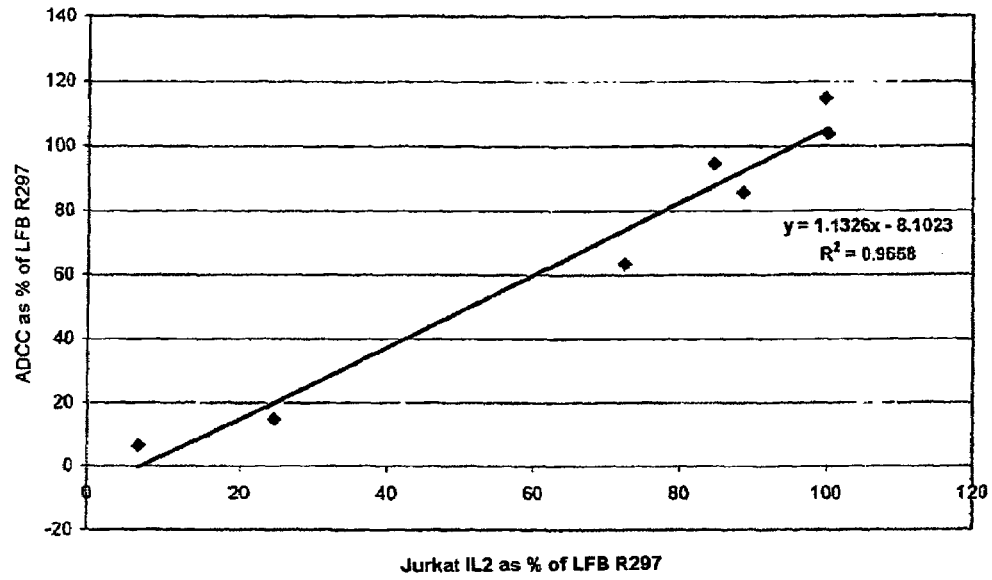
FIG. 10 shows a line of correlation between the ADCC (Tegelin 500 µg/well and anti-D at 7.5 ng/well) and the Jurkat IL2 assay.

FIG. 10: Line of correlation between the ADCC (Tegeline 500 µg/well and anti-D at 7.5 ng/well) and the Jurkat IL-2 assay.

Figure 11:
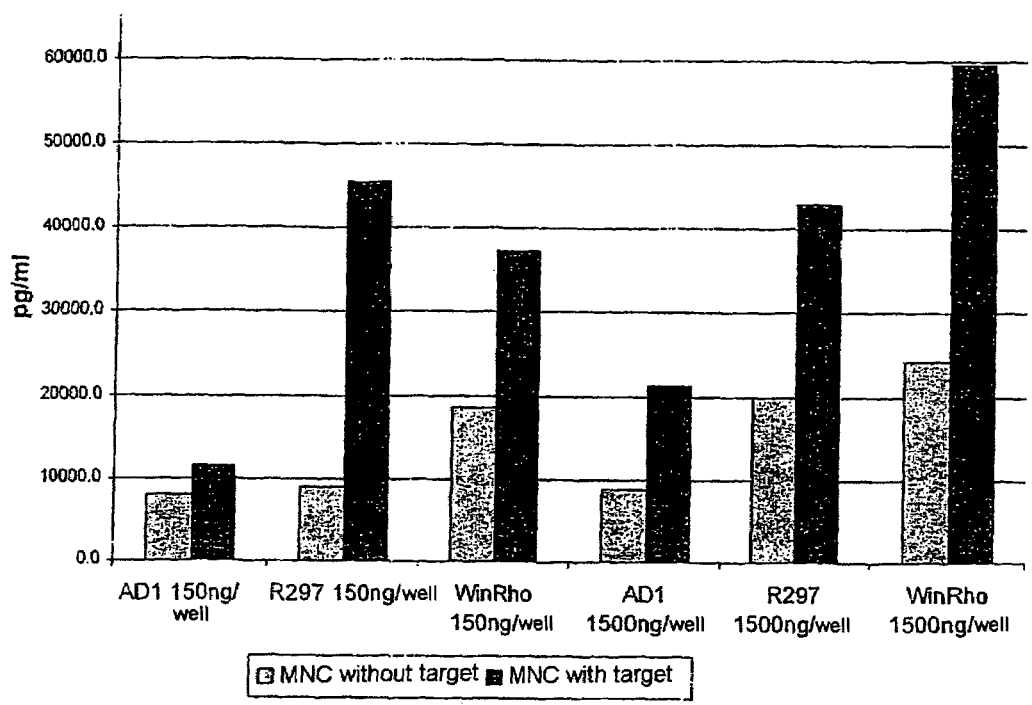
FIG. 11 show secretion of IL-8 by mononuclear cells.

FIG. 11: Secretion of IL-8 by mononuclear cells.

Figure 12:
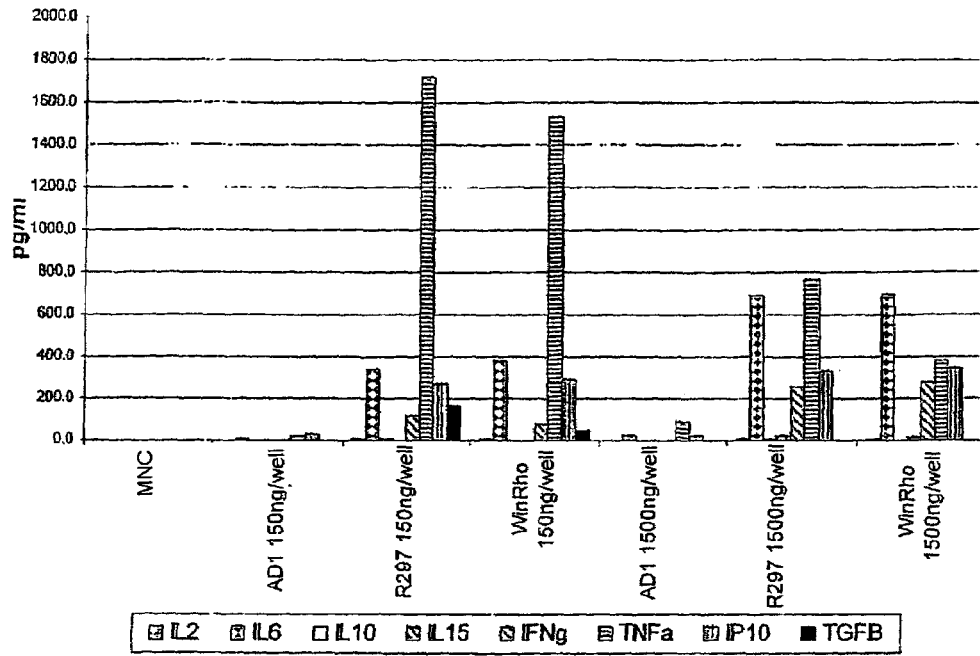
FIG. 12 shows induction of TNF alpha, IL-6 and TGF beta secretion by mononuclear cells.

FIG. 12: Induction of TNF alpha, IL-6 and TGF beta secretion by mononuclear cells.

Figure 13:
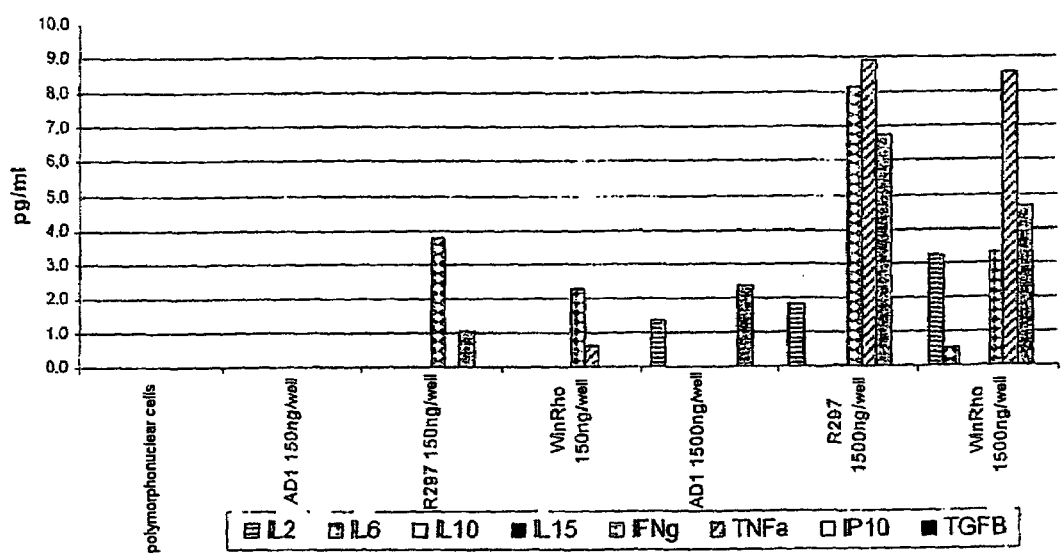
FIG. 13 shows induction of cytokine secretion by polymorphonuclear cells.

FIG. 13: Induction of cytokine secretion by polymorphonuclear cells.

Figure 14:
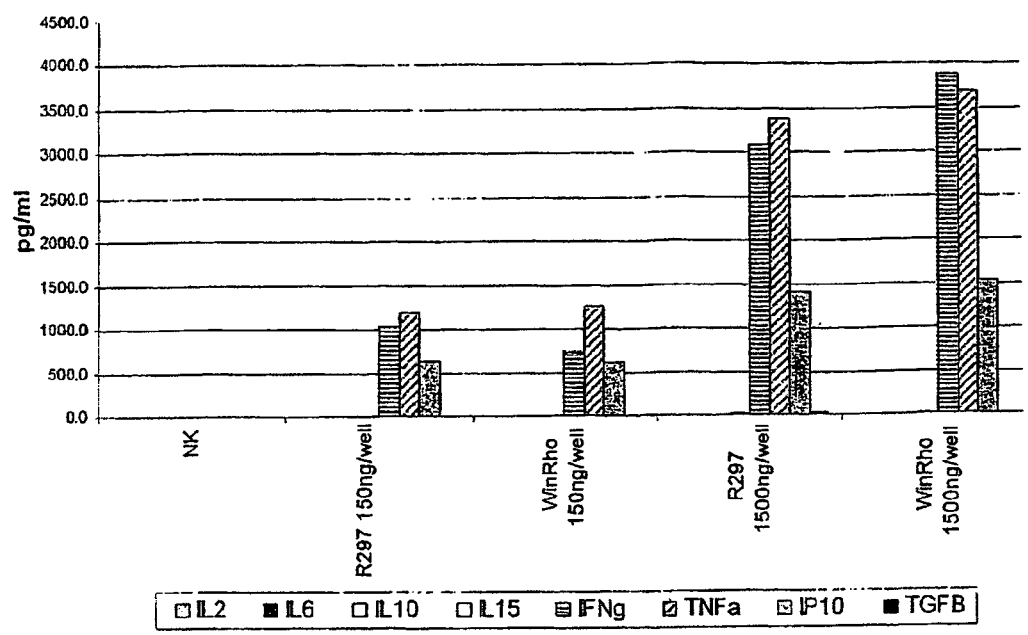
FIG. 14 shows induction of IFN gamma, TNF alpha and IP10 secretion by NK cells.

FIG. 14: Induction of IFN gamma, TNF alpha and IP10 secretion by NK cells.

FIG. 15: Secretion of TNF alpha by NK cells, induced by the anti-CD20 and anti-HLA-DR antibodies expressed in CHO and YB2/0 (324 03 082).

FIG. 16: Secretion of IFN gamma by NK cells, induced by the anti-CD20 and anti-HLA-DR antibodies expressed in CHO and YB2/0 (324 03 082).

EXAMPLE 1

Jurkat CD16 Assay

Antibodies:

WinRho polyclonal antibodies, DF5-EBV monoclonal antibody, DF5-YB2/0 monoclonal antibody.

Principle:

This assay evaluates the ability of the anti-D antibodies to bind to the CD16 receptor (Fc gamma RIII) expressed on Jurkat CD16 cells, and to induce IL-2 secretion.

This assay consists in bringing the following into contact in a 96-well plate: the anti-D antibodies, the papain-treated Rhesus-positive red blood cells, the Jurkat CD16 cells and PMA.

After an overnight incubation period at 37° C., the 96-well plates are centrifuged and the amount of secreted IL2 is assayed in the supernatant.

Material

Positive control antibodies: Poly-D WinRho, DF5-YB2/0.

Negative control antibody: DF5.

Rhesus-positive red blood cells.

Jurkat CD16 cells.

IL-2 assay kit: Quantikine from R/D.

Method

Treatment of red blood cells with papain.

1 ml of pellet of red blood cells diluted in PBS is incubated with 1 ml of a papain solution (1 mg/ml) for 10 min at 37° C. Three washes are then carried out in $H_2O$-0.15M NaCl.

Reaction mixture:

Antibody: 50 µl of a dilution to 150 ng/ml in IMDM 5% SVF,

PMA: 50 µl of a dilution to 40 ng/ml in IMDM 5% SVF, red blood cells treated with papain. 50 µl at $8 \times 10^6$/ml in IMDM 5% SVF, Jurkat CD16. 50 µl at $2 \times 10^6$/ml in IMDM 5% SVF.

Overnight incubation at 37° C.

Then, centrifugation of the plates, removal of 100 µl of supernatants and assaying of IL-2 with the commercial kit. Reading at 450 nm.

The values (in pg/ml) are given in the form of a histogram for each sample.

EXAMPLE 2

In Vitro Correlation Between ADCC and IL-2 Release by Jurkat CD16

For this study, 3 anti-D monoclonal antibodies were compared.

The Mab DF5-EBV was produced by human B lymphocytes obtained from a D-negative immunized donor, and immortalized by transformation with EBV. This antibody was used as a negative control given that it was shown to be incapable of eliminating Rhesus-positive red blood cells from the circulation in a clinical trial.

The monoclonal antibody (Mab) DF5-YB2/0 was obtained by expressing the primary sequence of DF5-EBV in the YB2/0 line. The monoclonal antibody R297 and other recombinant antibodies were also expressed in YB2/0.

These antibodies were assayed in vitro for their ability to induce lysis of papain-treated red blood cells using mononuclear cells (PBLs) as effector.

All the assays were carried out in the presence of human immunoglobulins (IVIgs) so as to reconstitute the physiological conditions.

It is thought that IVIgs bind with high affinity to FcgammaRI (CD64). The two Mabs DF5-YB2/0 and R297 induce red blood cell lysis at a level comparable with that of the WinRho antibodies. On the other hand, the Mab DF5-EBV is completely ineffective.

In a second series of experiments, purified NK cells and untreated red blood cells were used as effectors and targets, respectively. After incubation for 5 hours, the anti-D Mabs R297 and DF5-YB2/0 were shown to be capable of causing red blood cell lysis, whereas DF5-EBV remained ineffective.

In these two experiments, the red blood cell lysis was inhibited by the antibody 3G8 directed against FcgammaRIII (CD16).

In summary, these results demonstrate that the ADCC brought about by the antibody R297 and the antibody DF5-YB2/0 involves FcgammaRIII expressed at the surface of the NK cells.

In the context of the invention, a third series of experiments showed the value of an in vitro assay using Jurkat CD16 cells to evaluate the effectiveness of anti-D antibodies. The antibodies were incubated overnight with Rhesus-positive red blood cells and Jurkat CD16 cells. The release of IL-2 into the supernatant was evaluated by ELISA. A strong correlation between ADCC and activation of the Jurkat cells was observed, which implies that this assay can be used to discriminate between anti-D antibodies as a function of their reactivity toward FcgammaRIII (CD16).

The same samples are evaluated by ADCC and in the Jurkat IL-2 assay. The results are expressed as percentage of the reference antibody "LFB-R297". The curve for correlation between the two techniques has a coefficient of $r2=0.9658$ (FIG. 10).

In conclusion, these data show the importance of post-translational modifications of the structure of the antibodies in terms of their FcgammaRIII-specific ADCC activity. The release of cytokines such as IL-2 reflects this activity.

EXAMPLE 3

Activation of NK cells and Production of IL-2 and of IFNγ

Study model: NK cells purified from peripheral blood.
Applications: enhancement of an anti-tumor response.
IL-2 induces activation of T lymphocytes and of the NK cells themselves, which can go as far as stimulation of cell proliferation. IFNγ stimulates the activity of CTLs and can enhance the activity of macrophages.

EXAMPLE 4

Activation of Monocyte-Macrophages and Production of TNF and of IL-1Ra

Applications: Enhancement of phagocytosis and induction of anti-inflammatory properties. TNF stimulates the proliferation of tumor-infiltrating lymphocytes and macrophages. IL-1Ra is a cytokine produced by macrophages which compete with IL1 at the level of its receptor and thus exerts an anti-inflammatory effect.

EXAMPLE 5

Activation of Dendritic Cells and Production of IL10

Applications: Induction of tolerance specific to certain antigens. IL10 is a molecule that inhibits the activation of various effector cells and the production of cytokines.

EXAMPLE 6

Induction of Cytokine Secretion by Various Effector Cells

Three cell populations were studied: polymorphonuclear cells, mononuclear cells and NK cells. The cytokine syntheses are dependent on the presence of the target. There are few differences in the cytokine profiles induced by the antibody R297 and the polyclonal anti-D antibody. AD1 very often does not induce cytokine secretion.

Results:
6.1 The monoclonal antibody R297 and the polyclonal antibody WinRho induce considerable secretion of IL8 in the presence of mononuclear cells. This secretion is dependent on the antibody concentration and on the presence of the antigenic target. The antibody AD1 is much less effective (FIG. 11), i.e. less capable of inducing the production of cytokines.

With mononuclear cells (MNCs), the monoclonal antibody R297 and the polyclonal antibody WinRho induce considerable secretion of TNF alpha, and, to a lesser degree, although greater than AD1, secretion of IL6, of IFN gamma, of IP10, of TNF alpha and of TGF beta. At the highest antibody concentration, this secretion of IL6, IFN gamma and IP10 increases, but it decreases for TNF alpha and TGF beta (FIG. 12).

6.2 The monoclonal antibody R297 and the polyclonal antibody WinRho induce a very weak, but greater than AD1, secretion of IL-2, of IFN gamma, of IP10 and of TNF by polymorphonuclear cells. This secretion is antibody-concentration dependent (FIG. 13).

6.3 The monoclonal antibody R297 and the polyclonal antibody WinRho induce considerable secretion of IFN gamma, of IP10 and of TNF by NK cells. This secretion is antibody-concentration dependent (FIG. 14).

EXAMPLE 7

Optimized Chimeric Anti-CD20 and Anti-HLA-DR Antibodies Produced in YB2/0

Introduction
Our first results showed that the anti-D antibodies produced in YB2/0 and also the polyclonal antibodies used clinically induced the production of cytokines, in particular of TNF alpha and of interferon gamma (IFN gamma) from purified NK cells or from mononuclear cells. On the other hand, other anti-D antibodies, produced in other cell lines, are negative in ADCC and proved to be incapable of inducing this secretion.

The additional results below show that this mechanism is not exclusive to the anti-D antibodies in the presence of Rhesus-positive red blood cells, but also applies to the anti-CD20 and anti-HLA-DR antibodies expressed in YB2/0. Expression in CHO confers less substantial activating properties on the antibody. This is in correlation with the results obtained by ADCC.

Materials
Antibodies.
Anti-CD20: the chimeric anti-CD20 antibody transfected into YB2/0 is compared with a commercial anti-CD20 antibody produced in CHO (Rituxan).
Anti-HLA-DR: the same sequence encoding the chimeric anti-HLA-DR antibody is transfected into CHO (B11) or YB2/0 (4B7).
Target cells: Raji cells expressing at their surface the CD20 and HLA-DR antigens.
Effector cells: human NK cells purified by negative selection from a human blood bag.

Method
Various concentrations of anti-CD20 or anti-HLA-DR antibodies are incubated with Raji cells (targets) and NK cells (effectors). After incubation for 16 hours, the cells are centrifuged. The supernatants are assayed for TNF alpha and IFN gamma.

Results:

7.1 TNF alpha: The results are expressed in pg/ml of TNF alpha assayed in the supernatants. The various concentrations of antibodies added to the reaction mixture are given along the X-axis (FIG. 15).

The chimeric anti-CD20 and anti-HLA-DR antibodies produced in YB2/0 induce higher levels of TNF in the presence of their target (Raji) compared with the same antibodies produced in CHO. The amount of TNF alpha is clearly dose-dependent on the concentration of antibody added. At 10 mg/ml of antibody, five times more TNF alpha is induced with the antibodies produced in YB2/0 compared with the antibodies produced in CHO.

7.2 IFN gamma: The results are expressed in pg/ml of IFN gamma assayed in the supernatants. The various concentrations of antibodies added to the reaction mixture are given along the X-axis (FIG. 16).

The chimeric anti-CD20 and anti-HLA-DR antibodies produced in YB2/0 induce higher levels of IFN gamma in the presence of their target (Raji) compared with the same antibodies produced in CHO. The amount of IFN gamma is clearly dose-dependent on the concentration of antibody added. At all the concentrations used (0 to 200 ng/ml), the anti-HLA-DR antibody produced in CHO induces no secretion of IFN gamma, whereas 40 ng/ml of the antibody produced in YB2/0 induces approximately 1000 pg/ml of IFN gamma.

For the anti-CD20 antibody, less than 10 ng/ml of the antibody produced in YB2/0, and 200 ng/ml of the antibody produced in CHO, are required to induce 300 pg/ml of IFN gamma (FIG. 16).

REFERENCES

Jefferis, R., Lund, J., Mizutani, H., Nakagawa, H., Kawazoe, Y., Arata, Y. and Takahashi, N. A comparative study of the N-linked oligosaccharides structure of human IgG Subclass proteins. Biochem. J., 268:529-537 (1990).

Leatherbarrow, R. J., Rademacher, T. W., Dwek, R. A., Woof, J. M., Clark, A., Burton, D. R., Richardson, N. and Feinstein, A. Effector functions of monoclonal aglycosylated mouse IgG2a; binding and activation of complement component C1 and interaction with human Fc receptor. Molec. Immun. 22, 407-415 (1985).

Lund, J., Tanaka, T., Takahashi, N., Sarmay, G., Arata, Y. and Jefferis, R. A protein structural change in aglycosylated IgG3 correlates with loss of hu Fcγ RI and hu FcγRIII binding and/or activation. Molec. Immun. 27, 1145-1153 (1990).

Parekh, R. B., Dwek, R. A., Sutton, B. J., Fernandes, D. L., Leung, A., Stanworth, D., Rademacher, T. W., Mizuochi, T., Taniguchi, T., Matsuta, K., Takeuchi, F., Nagano, Y., Miyamoto, T. and Kobata, A. Association of rheumatoid arthritis and primary osteoarthritis with changes in the glycosylation pattern of total serum IgG. Nature, 316:452-457 (1985).

The invention claimed is:

1. A method for selecting a monoclonal antibody for increased ADCC activity, wherein said method comprises:
   a) bringing into contact in a reaction medium a Jurkat cell transformed with CD16, the monoclonal antibody, and the antigen for said antibody,
   b) measuring the amount of IL-2 cytokine released, and
   c) selecting an antibody for which the level of said IL-2 release is increased by more than 100% compared with a negative control, wherein the measurement of the amount of IL-2 is linearly correlated to the CD16-specific ADCC activity, and wherein the negative control is an antibody of the same specificity produced by CHO cells or the absence of the antibody.

* * * * *